United States Patent [19]

Hung et al.

[11] Patent Number: 5,214,167
[45] Date of Patent: May 25, 1993

[54] EPOXIDES AND THEIR PREPARATION

[75] Inventors: Ming-Hong Hung; Paul R. Resnick, both of Wilmington, Del.

[73] Assignee: E. I. Du Pont de Nemours and Company, Wilmington, Del.

[21] Appl. No.: 836,567

[22] Filed: Feb. 18, 1992

Related U.S. Application Data

[60] Continuation of Ser. No. 720,165, Jun. 27, 1991, abandoned, which is a division of Ser. No. 649,360, Feb. 1, 1991, abandoned, which is a division of Ser. No. 401,668, Aug. 30, 1989, Pat. No. 5,011,954.

[51] Int. Cl.$^5$ .................. C07D 301/02; C07D 317/10
[52] U.S. Cl. ...................... 549/518; 549/450; 549/455; 549/548
[58] Field of Search ............... 549/450, 455, 518, 548

[56] References Cited

U.S. PATENT DOCUMENTS

| | | | |
|---|---|---|---|
| 3,324,144 | 6/1967 | Coe et al. | 549/455 |
| 3,324,145 | 6/1967 | Madison | 549/455 |
| 3,749,791 | 7/1973 | Terrell et al. | 424/278 |
| 3,758,510 | 9/1973 | Delavarenne | 549/450 |
| 3,773,798 | 11/1973 | Neri et al. | 549/548 |
| 3,795,682 | 3/1974 | Delavarenne | 549/455 |
| 3,865,845 | 2/1975 | Resnick | 260/340.9 |
| 3,897,502 | 7/1975 | Russell et al. | 549/455 |
| 4,069,234 | 1/1978 | Wu | 549/518 |
| 4,111,965 | 9/1978 | Wu | 549/518 |
| 4,192,810 | 3/1980 | Wu | 549/518 |
| 4,257,966 | 3/1981 | Wu | 549/518 |
| 4,265,821 | 5/1981 | McEntire et al. | 549/518 |
| 4,276,223 | 6/1981 | Wu | 549/518 |
| 4,297,287 | 10/1981 | Costantini et al. | 549/518 |
| 4,374,259 | 2/1983 | McEntire | 549/518 |
| 4,393,227 | 7/1983 | Squire | 549/455 |
| 4,429,143 | 1/1984 | Anderson et al. | 549/455 |
| 4,496,750 | 1/1985 | Anderson et al. | 549/455 |
| 4,535,175 | 8/1985 | Squire | 549/455 |
| 4,731,356 | 3/1988 | Schulte-Elte et al. | 549/548 |
| 4,966,435 | 10/1990 | Matsumoto et al. | 549/455 |
| 5,011,954 | 4/1991 | Hung et al. | 549/455 |

FOREIGN PATENT DOCUMENTS 1045118 12/1978 Canada .

Primary Examiner—C. Warren Ivy
Assistant Examiner—A. A. Owens

[57] ABSTRACT

Process comprising heating a dioxole at 100°–400° C. for a sufficient time to convert the dioxole to an epoxide, for example, bis-2,2-trifluoromethyl-4,5-difluoro-1,3-dioxole to 2,3-epoxy-3-trifluoromethyl-4-trifluorobutyryl fluoride.

10 Claims, No Drawings

EPOXIDES AND THEIR PREPARATION

This is a continuation division of application Ser. No. 07/720,165, filed Jun. 27, 1991 abandoned which is a division of application Ser. No. 07/649,360 filed Feb. 1, 1991 abandoned as a division of application Ser. No. 07/401,668 filed Aug. 30, 1989 and issued Apr. 30, 1991 as U.S. Pat. No. 5,011,954.

BACKGROUND OF THE INVENTION

Field of the Invention

This invention relates to new fluorine-containing epoxides and the process of making them by the rearrangement of fluorine-containing dioxoles.

Background

The rearrangement of dioxolanes to epoxides containing functional groups has heretofore not been disclosed in the art. Such epoxides are useful for esterifying polyvinyl alcohol to make polymers having pendant fluorinated epoxy groups for use as membranes.

Resnick in U.S. Pat. No. 3,865,845 (commonly assigned) discloses

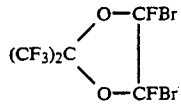

and a process for dehalogenating it to the perfluorodioxole using Zn.

Squire in U.S. Pat. No. 4,431,786 (commonly assigned) discloses halogenated dioxolanes and dioxoles, none of which contains bromine.

SUMMARY OF THE INVENTION

The present invention resides in a process for the rearrangement of the dioxole of the formula

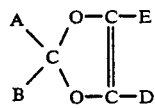

to the epoxide of the formula

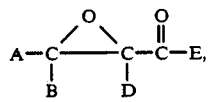

in which each of A and B is independently selected from $CF_3$, $CClF_2$, and $C_2F_5$; D is selected from H, $CF_3$, F, Cl, and Br; and E is selected from F, Cl and Br and, upon subsequent reaction of the epoxide as described hereinafter, COOR wherein R is lower alkyl, COOH and COOM wherein M is alkali metal. By "lower alkyl" is meant an alkyl group of 1–5 carbon atoms.

The invention herein also resides in new compositions of matter which are dioxoles, epoxides and dioxolanes.

DETAILED DESCRIPTION OF THE INVENTION

The rearrangement reaction of this invention is a simple, high yield, thermal rearrangement. It is surprising that such a reaction would occur, and especially that it would occur so smoothly. The reaction can be carried out batchwise under autogenous pressure, but it is preferable to conduct it continuously in the vapor phase by passing the dioxole through a hot tube. In the examples which are a part of this specification, batch reactions show yields as high as 83% and continuous reactions show yields as high as 93%. These yields are quite surprising, especially in view of the fact that handling losses are magnified when such small amounts of material as are used in the examples are reacted.

The reaction temperature for the rearrangement is 100°–400° C., preferably 225°–350° C. Longer reaction times are required at lower temperatures.

The reaction pressure is not critical. It is convenient to operate continuously at atmospheric pressure and to use autogenous pressure for batch reactions.

Diluents are not needed, but diluents which do not react with starting materials or products can be employed. Suitable diluents include perfluorocarbons and $CF_2Cl\text{-}CFCl_2$. It is desirable to keep moisture out of the reaction mixture.

The esterification of acid halides, as produced herein, is well known in the art. Esterification with methanol can be carried out at −50° C. to 100° C., preferably −10° C. to 25° C.

The conversion of one acid halide to another acid halide is well known in the art. Thus, E in the aforesaid formula for the epoxide can be converted from one halogen to another halogen. However, it is surprising and unexpected that a halogen exchange can be carried out without opening the epoxide ring.

Hydrolysis of the ester group may be carried out under mild conditions without attack on the epoxide group.

The direct bromination of 2,2-bis-trifluoromethyl-1,3-dioxolane can be carried out with bromine in the presence of cupric bromide, for example, as demonstrated in Examples 15 and 16. The temperature can be 100° C. to 350° C., preferably 175° C. to 300° C. The time required can range from 15 seconds to 8 hours, depending on the temperature, the extent of bromination desired, and whether the reaction is batch or continuous. Up to three bromine atoms can be introduced by direct bromination.

To obtain the tetrabromodioxolane (XX), HBr was removed from the tribromodioxolane (XVIII) of Example 16, using 50% aqueous NaOH and a quaternary ammonium salt. This gave the dibromodioxole (XIX) of Example 17, to which bromine was added in the presence of light to give the tetrabromodioxolane (XX) of Example 18.

One of the bromine atoms in the tetrabromodioxolane (XX) was replaced with F by reaction with HF and antimony pentachloride under conventional fluorination conditions, as described in Example 19. The resulting compound (XXI) of Example 19 was treated with Zn and bromine in dimethyl formamide to remove bromine and yield bis-2,2-trifluoromethyl-4-bromo-5-fluoro-1,3-dioxole (XXII), Example 20.

Removal of HBr from the bis-2,2-trifluoromethyl-4,5-dibromodioxolane (XVII) of Example 16 to give the corresponding 4-bromodioxole (XXIII) was carried out with 50% aqueous NaOH and a quaternary ammonium salt at room temperature (Example 21).

Examples 22–26 disclose conditions under which the known 2,2-bis-trifluoromethyl-4-hydroxymethyl-1,3- dioxolane can be converted by known reactions to 2,2,4-tris-trifluoromethyl-5-fluoro-1,3-dioxole (XXVIII), which can be rearranged according to the present invention (Example 27).

The dioxoles, epoxides and dioxolanes of this invention include:
the dioxole of the formula

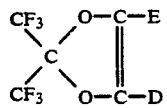

in which D is selected from H, F, Br and CF₃, and E is F or Br;
the epoxide of the formula

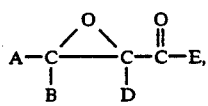

in which each of A and B is independently selected from CF₃, CClF₂, and C₂F₅; D is selected from H, CF₃, F, Cl, and Br; and E is selected from F, Cl, Br, COOR wherein R is lower alkyl, COOH, and COOM wherein M is alkali metal; and the dioxolane of the formula

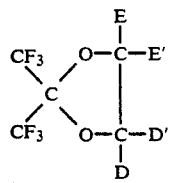

in which:
(a) each of D, D' and E is Br and E' is F;
(b) each of D, D', E and E' is Br;
(c) each of D, D' and E is Br and E' is H;
(d) each of D, D' and E' is H and E is Br;
(e) each of D and E is Br and each of D' and E' is H;
(f) each of D, D' and E is H and E' is COOH;
(g) each of D, D' and E is H and E' is CF₃;
(h) each of D, D' and E is Cl and E' is CF₃; or
(i) each of D and E is Cl, D' is F and E, is CF₃.

It is particularly surprising and unexpected that, in the aforesaid formula for the bis-2,2-trifluoromethyldioxole, when D is CF₃ and E is F, the rearrangement product is an epoxy acid fluoride rather than the expected epoxy ketone.

In the following examples, temperatures are in degrees Celsius.

EXAMPLE 1

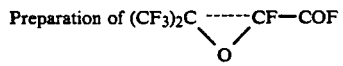

A one inch (2.5 cm) diameter glass tube twelve inches (30.5 cm) long was filled with glass beads, dried, heated to 280° and 17.4 g. of bis-2,2-trifluoromethyl-4,5-difluoro-1,3-dioxole was added at a rate of 0.48 mL per minute to give 15.0 g. of a colorless liquid, boiling at 35° The infrared spectrum [C=0 1887 cm.⁻¹, oxirane 1462 cm⁻¹] and the ¹⁹F NMR spectrum [+28.7(1F), −68.9(3F), −71.1(3F), −148.6(1F )] are consistent with structure (I).

EXAMPLE 2

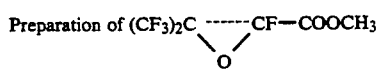

Anhydrous methanol, 10 mL, was added to 18 g. of cold (I). The reaction mixture was washed with 200 mL water and the lower layer distilled to give 12.0 g. (II), boiling at 91°. The infrared spectrum [C=0 1792 cm.⁻¹, oxirane 1464 cm⁻¹] and the NMR spectra [¹H 3.80; ¹⁹F −68.6 (3F), −71.3 (3F), −145.8 (1F)] are Consistent with structure (II).

EXAMPLE 3

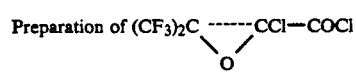

In the same manner as in Example 1, 48.7 g. of bis-2,2-trifluoromethyl-4,5-dichloro-1,3-dioxole was added at a rate of 0.48 mL per minute to give 47.2 g. of product. The combined product of two runs was distilled to give 87.0 g. (III) boiling at 92°. The infrared spectrum [C=0 1821 cm. ⁻¹, oxirane 1418 cm. ⁻¹] and the 19F NMR spectrum [−66.5 q., −69.3 q. J=8.5 Hz.] were consistent with structure (III).

EXAMPLE 4

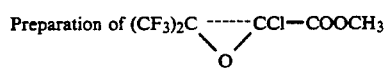

In the same manner as in Example 2, 87.0 g. (III) was treated with 50 mL anhydrous methanol to give 72.0 g. (IV), boiling at 120°. The infrared spectrum [C=0 1805 cm. ⁻¹, oxirane 1445 cm. ⁻¹] and NMR spectrum [¹H 3.83; ¹⁹F −66.3 (3F), −70.5 (3F)] were consistent with structure (IV).

EXAMPLE 5

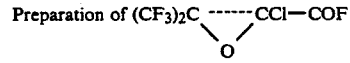

a) A sealed glass tube containing 1.7 g. bis-2,2-trifluoromethyl-4-fluoro-5-chloro-1,3-dioxole was heated at 200 for 16 hours. The 1.6 g. product contained 88% (V). The infrared spectrum [C=0 1887 cm. ⁻¹, oxirane 1431 cm. ⁻¹] and the 19F NMR spectrum [+25.0 (1F), −67.6 (3F), −71.2 (3F)] were consistent with the proposed structure. Reaction of (V) with methanol gave (IV) as the only product.

b) In the same manner as in Example 1, 12.8 g. of S bis-2,2-trifluoromethyl-4-fluoro-5-chloro-1,3-dioxole was added at a rate of 0.48 mL per minute to give 12.4 g. of product containing 96% (V).

EXAMPLE 6

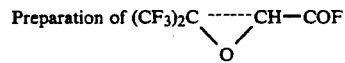

In the same manner as in Example 1, 11.7 g. of bis-2,2-trifluoromethyl-4-fluoro-1,3-dioxole was added at a rate of 0.48 mL per minute to give 10.8 g. of product. Distillation gave 7.8 g. of (VI) boiling at 73°. The infrared spectrum [C=O 1894, 1869 cm.$^{-1}$, oxirane 1460 cm.$^{-1}$] and NMR spectrum [1H 4.18; $^{19}$F +37.8 (1F), −69.8 (3F), −74.5 (3F)] were consistent with structure (VI).

EXAMPLE 7

Preparation of (CF$_3$)$_2$C─────CH─COOCH$_3$  (VII)
        \\O/

In the same manner as in Example 2, 1.18 g. (VI) was treated with one mL methanol to give 1.25 g. (VII) boiling at 106°. The infrared spectrum [C=O 1786 cm.$^{-1}$, oxirane 1449 cm.$^{-1}$] and the NMR spectrum [$^1$H 3 74 (3H), 4.13 (2H); $^{19}$F −70.0 (3F), −74.3 (3F)] were consistent with structure (VII).

EXAMPLE 8

Preparation of (CClF$_2$)$_2$C─────CCl─COCl  (VIII)
        \\O/

In the same manner as in Example 1, 23.5 g. bis-2,2-chlorodifluoromethyl-4,5-dichlorodioxole was added at 300° at the rate of 0.64 g. per minute to give 23.0 g. of a pale yellow liquid. Distillation yielded 20.2 g. (VIII) boiling at 147°. The infrared spectrum [C=O 1792 cm.$^{-1}$, oxirane 1404 cm.$^{-1}$] was consistent with structure (VIII).

EXAMPLE 9

Preparation of (CClF$_2$)$_2$C─────CCl─COOCH$_3$  (IX)
        \\O/

In the same manner as in Example 2, 4.9 g. (VIII) was treated with three mL of anhydrous methanol to give 4.0 g. (IX) boiling at 179°. The infrared spectrum [C=O 1776 cm.$^{-1}$, oxirane 1447 cm.$^{-1}$] and the NMR spectrum [$^1$H 3.85; $^{19}$F −54.0] were consistent with structure (IX).

EXAMPLE 10

Preparation of (CF$_3$)$_2$C─────CBr─COBr  (X)
        \\O/

A mixture or 31.5 g. bis-2,2-trifluoromethyl-1,3-dioxole and 96 g. bromine was heated at 250° for one hour. The product was distilled to give 3.2 g. of material boiling at 54° at 50 torr which contained 52 mole percent (X). The infrared spectrum [C=O 1800 cm.$^{-1}$, oxirane 1420 cm.$^{-1}$] and the $^{19}$F NMR spectrum [−66.1 (3F) and −68.2 (3F)] were consistent with structure (X).

EXAMPLE 11

Preparation of (CF$_3$)$_2$C─────CBr─COOCH$_3$  (XI)
        \\O/

In the same manner as in Example 1, 10.6 g. of bis-2,2-trifluoromethyl-4,5-dibromo-1,3-dioxole was added at a rate of 0.57 mL per minute to give 8.86 g. of product mixture containing (X). Treatment with methanol as in Example 2 yielded 6.0 g. of material. Distillation gave 2.5 g. (XI) boiling at 135°. The infrared spectrum [C=O 1791 cm.$^{-1}$, oxirane 1445 cm.$^{-1}$] and the NMR spectrum [1H 3.97; $^{19}$F −65.8 (3F), −70.1 (3F)] were consistent with structure (XI).

EXAMPLE 12

Preparation of (CF$_3$CF$_2$)$_2$C─────CF─COF  (XII)
        \\O/

A sealed glass tubing containing 1.0 g bis-2,2-pentafluoroethyl-4,5-difluoro-1,3-dioxole was heated at 220° for 15.5 hours. The 0.5 g. liquid product was mostly (XII). The infrared spectrum [C=O 1894 cm. $^{-1}$, oxirane 1435 cm.$^{-1}$] and $^{19}$F NMR spectrum [+28 (1F), −82 (6F), −113 (4F), −146 (1F)] were consistent with structure (XII).

EXAMPLE 13

Preparation of (CF$_3$CF$_2$)$_2$C─────CF─COOCH$_3$  (XIII)
        \\O/

The product (XII) of Example 12 was treated with methanol in the manner of Example 2. The major component of the product, (XIII), was separated chromatographically. The $^{19}$F NMR of this material [−75.3 (3F), −76.0 (3F), −107.6 (complex) (4F), −136.4 (1F)] was in agreement with structure (XIII).

EXAMPLE 14

Preparation of (CF$_3$)$_2$C─────CF─COOM  (XIV) M = H
        \\O/        (XV) M = Na a) A tube containing 14.5 g. bis-2,2-trifluoromethyl-4,5-difluoro-1,3-dioxole was heated at 100 for 30 minutes, 150 for 30 minutes and 200° for 30 minutes. The major component of the crude product was (I). The product was shaken with 5% aqueous sodium bicarbonate, extracted with CFC-113, trichlorotrifluoroethane, acidified with aqueous hydrochloric acid and extracted with ether. The ether layer was distilled to give (XIV) boiling at 74° at 50 torr. The infrared spectrum [C=O 1754 cm.$^{-1}$] and the $^{19}$F NMR spectrum [−68.5 (3F), −70.8 (3F), −146.8 (1F)] were consistent with structure (XIV).

b) The above acid, (XIV), was dissolved in 10 mL water, neutralized with 1.0N sodium hydroxide and the water was evaporated to give a white solid, (XV) The $^{19}$F NMR spectrum [−65.7 (3F), −68.5 (3F), −142.9 (1F)] was consistent with structure (XV).

EXAMPLE 15

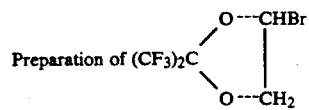

Preparation of (CF$_3$)$_2$C with O---CHBr and O---CH$_2$ (XVI)

A mixture of 3.0 g. cupric bromide, 16.0 g. bromine and 21.0 g. S bis-2,2-trifluoromethyl-1,3-dioxolane was heated at 225° for two hours. The crude product was added to water, washed with aqueous sodium bisulfite and distilled to give 1.0 g. (XVI) boiling at 52° at 50 torr. The infrared and $^1$H NMR spectrum [4.85 (2H), 6.67 (1H)] were consistent with structure (XVI).

EXAMPLE 16

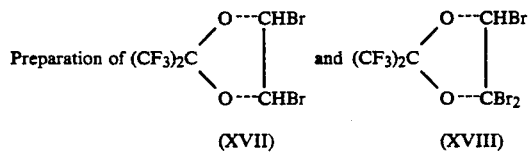

Preparation of (XVII) and (XVIII)

a) A mixture of 3.0 g. cupric bromide, 10.5 g. bis-2,2-trifluoromethyl-1,3-dioxolane and 32.0 g. bromine was heated at 225° for two hours. The crude product was added to water and washed with aqueous sodium bisulfite to give 14.7 g. of a colorless liquid. Distillation yielded 1.1 g. (XVII) boiling at 67° at 50 torr and 6.3 g. (XVIII) boiling at 88° at 50 torr. The infrared spectrum and NMR spectrum [$^1$H 6.95; $^{19}$F −78.3] were consistent with structure (XVII). The infrared spectrum and NMR spectrum [$^1$H 7.43; 19F −77.2 (3F), −78.3 (3F)] were consistent with structure (XVIII).

b) A 15.6 g. mixture of bis-2,2-trifluoromethyl-1,3-dioxole (65%) and bis-2,2-trifluoromethyl-4-chloro-1,3-dioxole (35%) and excess bromine was irradiated with a sun lamp for 25 minutes. The excess bromine was destroyed by reaction with aqueous sodium bisulfite and the 24.3 g. product was distilled to give (XVII) boiling at 69° at 50 torr. and whose infrared and NMR spectra were the same as those of (XVII) prepared above.

Bis-2,2-trifluoromethyl-4,5-dibromo-5-chloro-1,3-dioxolane boiling at 78° at 50 torr. was isolated from the higher boiling material. The structure of this material was consistent with the NMR spectrum [$^1$H 7.29; 19F −77.6 (3F), −78.4 (3F)].

EXAMPLE 17

Preparation of Bis-2,2-trifluoromethyl-4,5-dibromo-1,3-dioxole (XIX)

A mixture of 85 mL 50% aqueous sodium hydroxide, 82.0 g. (XVIII) and five drops (CH$_3$—CHOH—CH$_2$)$_2$N(CH$_2$C$_6$H$_5$)C$_{12}$H$_{25}$+Cl$^-$ was stirred at room temperature for 18 hours. The reaction mixture was added to water and the lower layer washed with an equal volume of water to give 54.2 g. product. Distillation yielded 51.9 g. (XIX), b. p. 62° at 100 mm. The infrared spectrum and $^{19}$F NMR spectrum [−82.3] were consistent with structure (XIX).

EXAMPLE 18

Preparation of Bis-2,2-trifluoromethyl-4,5,5-tetrabromo-1,3-dioxolane (XX)

Bromine was slowly added to 51.5 g. (XIX) while irradiating with a sun lamp. Excess bromine was added and the irradiation continued for 20 minutes. The remaining bromine was destroyed with aqueous sodium bisulfite and the product was distilled to give (XX) boiling at 86° at 10 torr. The infrared and $^{19}$F NMR spectra [−75.0] were consistent with structure (XX).

EXAMPLE 19

Preparation of Bis-2,2-trifluoromethyl-4,4,5-tribromo-5-fluoro-1,3-dioxolane (XXI)

A mixture of 20.0 g. (XX), 1.0 g. antimony pentachloride and 10 g. anhydrous hydrogen fluoride was heated at 70° for one hour and 100° for one hour. The reaction mixture was added to water and the lower layer was distilled to give (XXI) boiling at 48° at 10 torr and unconverted (XX). The $^{19}$F NMR [−27.5 (1F), −77.3 (3F), −78.7 (3F)] was consistent with structure (XXI).

EXAMPLE 20

Preparation of Bis-2,2-trifluoromethyl-4-bromo-5-fluoro-1,3-dioxole (XXII)

A mixture of 5.0 g. zinc and 30 mL dimethylformamide was stirred at 27° and 0.5 g. bromine was added. The mixture was cooled to room temperature and 23.2 g. (XXI) was added. The temperature rose to 75°. The mixture was cooled to room temperature and distilled to give 7.5 g. of product containing 43% (XXII) which was isolated chromatographically. The infrared spectrum [1790 cm. $^{-1}$] and the $^{19}$F NMR spectrum [−83.4 (6F), −149.7 (1F)] were consistent with structure (XXII).

EXAMPLE 21

Preparation of Bis-2,2-trifluoromethyl-4-bromo-1,3-dioxole (XXIII)

A mixture of 15.6 g. (XVII), 15 mL 50% aqueous sodium hydroxide and 3 drops (CH$_3$—CHOH—CH$_2$)$_2$N(CH$_2$C$_6$H$_5$)C$_{12}$H$_{25}$+Cl$^-$ was stirred at room temperature for 17 hours. The reaction mixture was added to water and the lower layer was washed with an equal volume of water to give 6.9 g. product. (XXIII) was separated chromatographically from the mixture and the infrared and NMR spectra [$^1$H 6.69; $^{19}$F −82.3] were consistent with the dioxole structure (XXIII).

EXAMPLE 22

Preparation of 2,2-Bis-trifluoromethyl-4-carboxy-1,3-dioxolane (XXIV)

A mixture of 48.0 g. A 2,2-bis-trifluoromethyl-4-hydroxymethyl-1,3-dioxolane (made according to either U.S. Pat. No. 3,758,510 or U.S. Pat. No. 3,795,682), 180 mL water and 36.0 g. sodium carbonate was stirred and 63.2 g. of potassium permanganate was added slowly while the temperature was kept below 30° After stirring at room temperature for 16 hours sodium bisulfite was added to reduce the excess potassium permanganate to manganese dioxide. The resulting mixture was filtered, the filtrate was made basic with saturated sodium carbonate solution, extracted with ether, neutralized with hydrochloric acid, extracted with ether and the solvent was removed to give 28.0 g. (XXIV), m.p. 62°–63°. The NMR spectra [$^{19}$F −79.8, −80.3 ; $^1$H 10.3, 5.22, 4.83, 4.59] were consistent with structure (XXIV).

EXAMPLE 23

Preparation of 2,2,4-Tris-trifluoromethyl-1,3-dioxolane (XXV)

A mixture of 12.7 g. (XXIV), 16.2 g. sulfur tetrafluoride and 10 g. anhydrous hydrogen fluoride was heated at 85° for 6 hours. The product was distilled to give 8.0 g. (XXV), boiling at 36° at 110 torr. The NMR spectra [$^{19}$F −79.0 (3F), −80.7 (3F), −81.5 (3F); $^1$H 4.42 (2H), 4.73 (1H)] were consistent with structure (XXV).

EXAMPLE 24

Preparation of 2,2,4-Tris-trifluoromethyl-4,5,5-trichloro-1,3-dioxolane (XXVI)

Chlorine was added to 20 g. (XXV) at approximately 120° while irradiating with a sunlamp until there was no further reaction. The product was distilled to give 24.0 g. (XXVI) as a colorless liquid boiling at 80 at 160 torr. The $^{19}$F NMR spectrum [−74.2 (3F), −78.0 (3F), −78.5 (3F)] was consistent with structure (XXVI).

EXAMPLE 25

Preparation of 2,2,4-Tris-trifluoromethyl-4,5-dichloro-5-fluoro-1,3-dioxolane (XXVII)

A mixture of 21.0 g. (XXVI), 13.6 g. antimony trifluoride, and 8.5 g. antimony pentachloride was heated at 100°–110° for 8 hours. The product was distilled at 40° at 32 torr. and washed with saturated aqueous sodium bicarbonate to give 14.0 g. (XXVII). The $^{19}$F NMR spectrum [trans isomer −40.7 (1F), −77.3 (3F), −79.5 (3F), -80.7 (3F); cis isomer −54.3 (1F), −77.0 (3F), −79.2 (3F), −80.7 (3F)] was consistent with structure (XXVII).

EXAMPLE 26

Preparation of 2,2,4-Tris-trifluoromethyl-5-fluoro-1,3-dioxole (XXVIII)

A suspension of 2.5 g. lithium aluminum hydride in 40 mL tetrahydrofuran was cooled and treated with 3.12 g. titanium tetrachloride. The mixture was heated to reflux for 30 minutes, cooled and 12.0 g. (XXVII) added slowly to keep the reaction temperature between 27° and 35°. The reaction mixture was distilled, and the distillate was washed with water to obtain 8.5 g. (XXVIII) boiling at 42°. The $^{19}$F NMR [−68.6 (3F), −84.2 (6F), −136.8 (1F)] was consistent with structure (XXVIII).

EXAMPLE 27

Preparation of 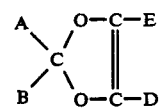 (XXIX)

A sealed glass tube containing 2.0 g. (XXVIII) was heated at 200° for 15 minutes and 240° for 30 minutes. The $^{19}$F NMR of the product showed that no (XXVIII) remained. (XXIX) was the sole product, $^{19}$F NMR [+37.7 (1F, COF), −66.7 (3F), −68.0 (3F), −71.3 (3F)].

EXAMPLE 28

Preparation of 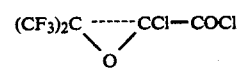 (V)

A one inch (2.5 cm) diameter glass tube twelve inches (30.5 cm) long was filled halfway with potassium fluoride powder, dried in a stream of nitrogen at 100 for 12 hours, then at 250° and 13.2 g. bis-2,2-trifluoromethyl-4,5-dichloro-1,3-dioxole added at 250 in 4.95 minutes. The product was a mixture of the starting dioxole, (III) and (V). Addition of methanol to an aliquot of the product gave (IV) and the starting dioxole.

A mixture of 5.8 g. potassium fluoride, 35 mL diglyme and 11.1 g. of the above product containing the starting dioxole, (III) and (V) was heated to give 8.2 g. of distillate which was a mixture of the starting dioxole and (V). No (III) remained.

A 2.2 g. sample of the starting dioxole and (V) from the previous reaction was heated in a sealed tube at 275 for one hour. The product contained only (III) and (V). No starting dioxole remained.

This example shows that

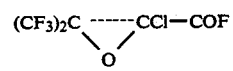 (III)

can be reacted with KF to give

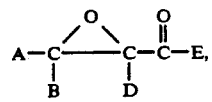 (V)

without opening of the epoxide ring.

We claim:

1. Process for rearrangement of the dioxole of the formula $$\begin{array}{c} A \\ \diagdown \\ B \diagup \end{array} C \begin{array}{c} O-C-E \\ \diagdown \quad \parallel \\ \diagup \\ O-C-D \end{array}$$

to the epoxide of the formula $$A-\underset{B}{\overset{}{C}} \overset{O}{\diagdown} \underset{D}{\overset{}{C}} - \overset{O}{\underset{\parallel}{C}} - E,$$

in which each of A and B is independently selected from $CF_3$, $CClF_2$, and $C_2F_5$; D is selected from H, $CF_3$, F, Cl, and Br; and E is selected from F, Cl, and Br, the process comprising heating the dioxole at 100°–400° C. for a time sufficient to carry out the rearrangement.

2. The process of claim 1 in which the heating is carried out at 225°–350° C.

3. The process of claim 1 in which the reaction is carried out continuously in the vapor phase.

4. The process of claim 1 in which the reaction is carried out batchwise under autogenous pressure.

5. The dioxole of the formula

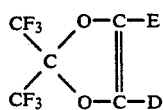

in which D is selected from Br and CF$_3$, and E is F or Br.

6. The dioxole of claim 5 in which D is Br and E is F.
7. The dioxole of claim 6 in which D is Br and E is Br.
8. The dioxole of claim 6 in which D is CF$_3$ and E is F.
9. The dioxole of claim 6 in which D is CF$_3$ and E is Br.
10. The dioxolane of the formula

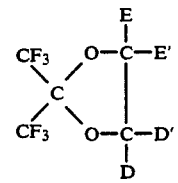

in which:
(a) each of D, D' and E is Br and E' is F;
(b) each of D, D', E and E' is Br;
(c) each of D, D' and E is Br and E' is H;
(d) each of D, D' and E' is H and E is Br;
(e) each of D, D' and E is H and E' is COOH;
(f) each of D, D' and E is H and E' is CF$_3$;
(g) each of D, D' and E is Cl and E' is CF$_3$; or
(h) each of D and E is Cl, D' is F and E' is CF$_3$.

* * * * *